United States Patent [19]

Liang et al.

[11] Patent Number: 5,069,546

[45] Date of Patent: Dec. 3, 1991

[54] ATMOSPHERIC PRESSURE CAPACITIVELY COUPLED PLASMA SPECTRAL LAMP

[75] Inventors: Dong C. Liang, Vancouver; Michael W. Blades, Surrey, both of Canada

[73] Assignee: University of British Columbia, Vancouver, Canada

[21] Appl. No.: 401,181

[22] Filed: Aug. 31, 1989

[51] Int. Cl.[5] .................................................. G01N 21/73
[52] U.S. Cl. .................................. 356/316; 315/111.21
[58] Field of Search ....................... 356/316; 315/111.21

[56] References Cited

U.S. PATENT DOCUMENTS 4,479,075 10/1984 Elliott ............................. 315/111.21

OTHER PUBLICATIONS

D. C. Liang & M. W. Blades, Anal. Chem., vol. 60, No. 1, 27 (1988).
D. C. Liang & M. W. Blades, Abstracts, The Pittsburgh Conference & Exposition, Paper No. 415 & 1140 (1988).
Improved Hollow Cathode Lamps for Atomis Spectroscopy 1985, Ed. S. Caroli, Ellis Horwood Limited.
J. A. C. Broekaert, J. Anal. At. Spectrom 2, 537 (1987).
G. Gillson & G. Horlick, Spectrochim. Acta 41B, 431 (1986).
P. Hannaford & A. Walsh, Spectrochim. Acta 43B, 1053 (1988).
H. J. Kim & E. H. Piepmeier, Anal. Chem. 60, 2040 (1988).
A. E. Bernhard, Spectroscopy, 2 No. 6, 24 (1987).
B. Chapman, Transactions of the Conference and School on the Elements, Techniques and Applications of Sputtering, 1 (1969).
G. K. Wehner, Advances in Electronics and Electron Phys., 7, 239 (1955).
G. S. Anderson, W. N. Mayer & G. K. Wehner, J. Appl. Phys., 33, 2991 (1962).
R. Stephens, J. Anal. At. Spectrom. 3, 1137 (1988).

Primary Examiner—F. L. Evans
Attorney, Agent, or Firm—Barrigar & Oyen

[57] ABSTRACT

A atmospheric pressure capacitively coupled plasma high intensity spectral lamp. The lamp generates atom line and ion line spectra from a substance to be analyzed. The lamp comprises a hollow means adapted for containing and sustaining an atmospheric pressure capacitively generated plasma discharge, a first electrode connected to a radio frequency power supply, electrically insulated from the plasma and enclosing at least a portion of the hollow means, and a second electrode constructed of the substance to be analyzed, connected to a radio frequency power supply, the electrode penetrating into the plasma discharge and being capacitively arranged with the first electrode.

14 Claims, 3 Drawing Sheets

U.S. Patent   Dec. 3, 1991   Sheet 1 of 3   5,069,546
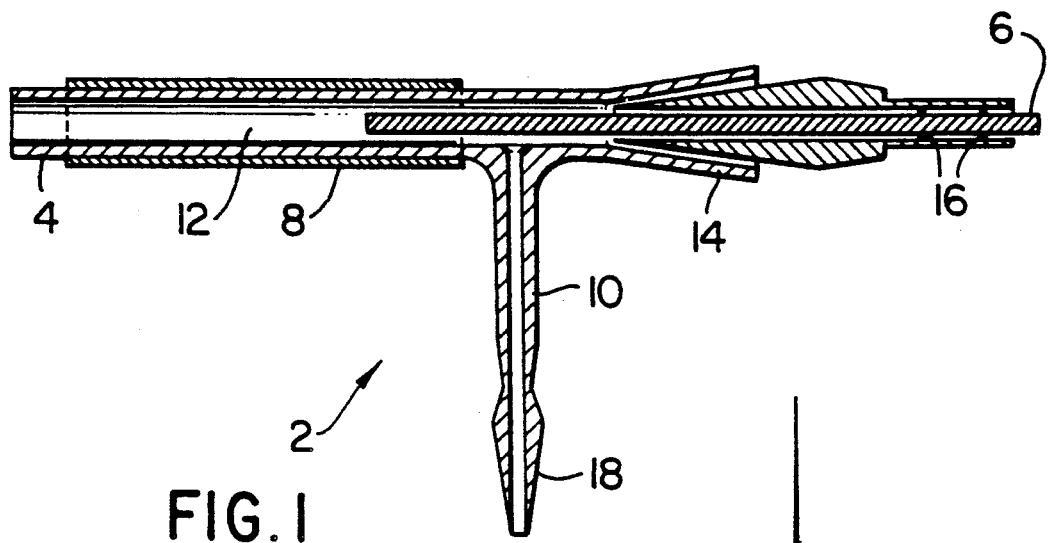
FIG.1
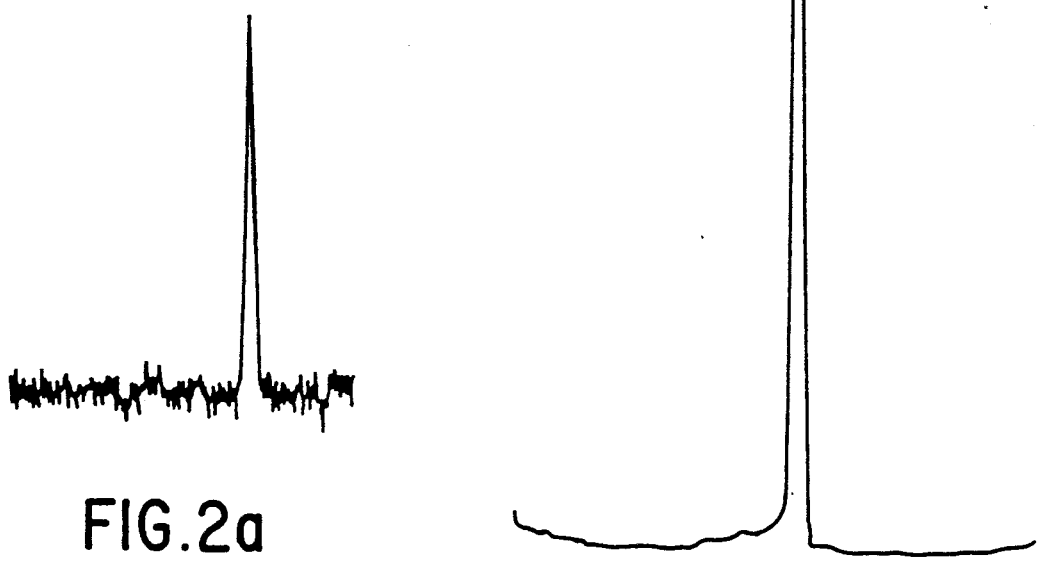
FIG.2a
FIG.2b

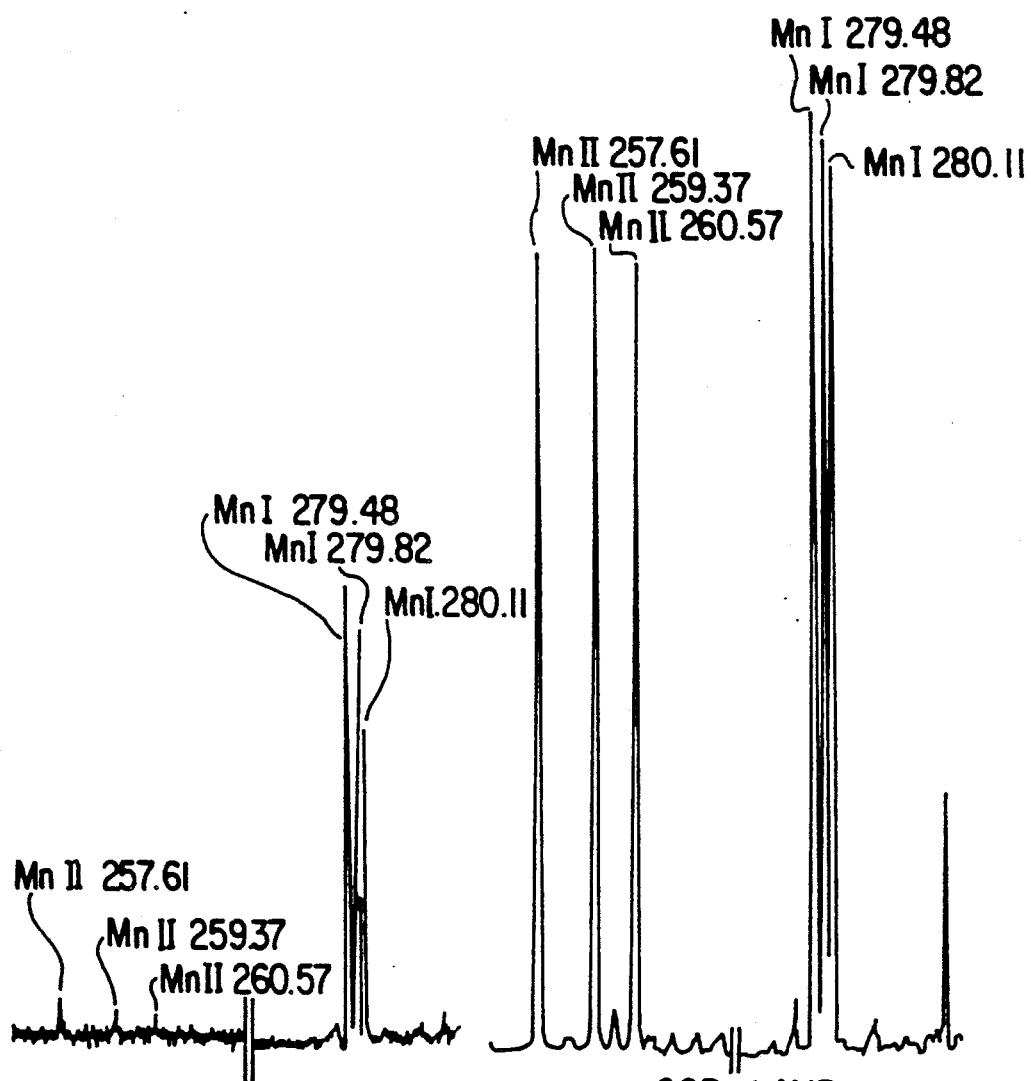

ATMOSPHERIC PRESSURE CAPACITIVELY COUPLED PLASMA SPECTRAL LAMP

FIELD OF THE INVENTION

This application relates to a novel atmospheric pressure capacitively coupled plasma high intensity spectral lamp.

BACKGROUND OF THE INVENTION

The development and characterization of an atmospheric pressure, capacitively coupled plasma (CCP) torch for atomic absorption spectrometry (AAS) has been specifically described [D. C. Liang and M. W. Blades, Anal. Chem. 60, 27 (1988)]. Subsequent work has demonstrated that this device can also be used quite effectively as a source for atomic emission spectrometry (AES) [D. C. Liang and M. W. Blades, Abstracts, The Pittsburgh Conference & Exposition, paper No. 415 and 1140 (1988)]. The configuration described previously was designed for the analysis of small volumes of liquid samples of a size typically analyzed by electrothermal atomization AAS (5–50 $\mu$L). However, the CCP can also be combined with other sample introduction techniques including laser ablation. The CCP developed for AAS was characterized by a long path length (20 cm) small diameter plasma sustained by capacitive coupling. The plasma could be operated at support-gas flow rates as low as 0.2 L/m and at radio frequency (rf) input powers between 30 to 600 W. Both the long path length tube geometry of the discharge and low support-gas flow rates acted to maximize analyte residence time in the plasma resulting in detection limits in the ng/L range.

By far the most important commercial spectral lamp for AAS and AFS is the hollow cathode lamp (HCL). The main advantages of the HCL are its very small spectral line-width and its high signal to background ratio. However, the absolute intensity of emission from the HCL is relatively low compared with the radiation from other plasma sources. To overcome this problem techniques such as direct current (dc) boosted-HCL, rf boosted-HCL, microwave coupled HCL, and high current pulsed HCL have been developed [Improved Hollow Cathode Lamps for Atomic Spectroscopy 1985, Ed. S. Caroli, Ellis Horwood Limited]. Additionally, the intensities of ion lines in HCLs are very weak, due to the dominant population of ground state atom in glow discharges [J. A. C. Broekaert, J. Anal. At. Spectrom. 2, 537 (1987)]. Traditional AAS primarily makes use of atomic resonance lines; however there is a large population of ground state analyte ions in ICP's even at relatively low powers [G. Gillson and G. Horlick, Spectrochim. Acta 41B, 431 (1986)]. The development of an intense ion line spectral source has some significance in this area in that it could assist in the reduction of source induced shot noise, consequently improving the detection limits for plasma source AAS.

There has recently been much interest in the application of sputtering sources in atomic spectrometry [P. Hannaford and A. Walsh, Spectrochim. Acta 43B, 1053 (1988)] [H. J. Kim and E. H. Piepmeier, Anal. Chem. 60, 2040 (1988)] [A. E. Bernhard, Spectroscopy, 2 No. 6, 24 (1987)]. Sputtering is the ejection of material from a surface caused by bombardment with an energetic beam of particles [B. Chapman, in Transactions of the Conference and School on the Elements, Techniques and applications of sputtering, 1 (1969)]. DC sputtering in a glow discharge source allows one to analyze solid samples by atomizing the analytes directly from the solid state. This approach offers some advantages. The time-consuming sample decomposition step can be omitted and analysis can be carried out without addition of reagents and without any separation and/or concentration steps so the risks of introducing contaminants and the loss of the element to be determined are considerably reduced. As a consequence an analysis can be carried out quite rapidly. It would appear that the sputtering rate should be a direct function of gas pressure, since the higher the pressure the more ions which would be available for sputtering. However, sputtering is usually carried out at pressures between $5 \times 10^{-3}$ and 1 torr since glow discharges extinguish or switch over to arc discharges at higher pressures and the main sampling mechanism in arcs is thermal evaporation.

Although rf sputtering is not widely used as a sample introduction method in atomic spectroscopy, it has long been recognized as an important technique in sputter etching and chemical vapour deposition [B. Chapman, in Transactions of the Conference and School on the Elements, Techniques and applications of sputtering, 1 (1969)]. Rf sputtering at low pressures first suggested by Wehner in 1955 [G. K. Wehner, Advances in Electronics and Electron Phys., 7, 239 (1955)] and demonstrated in 1962 [G. S. Anderson, W. N. Mayer and G. K. Wehner, J. Appl. Phys., 33,2991 (1962)] has become a standard method for etching materials in the semiconductor industry. Atmospheric pressure rf sputtering was previously used by the inventors to supply Fe to the CCP discharge for the purpose of making temperature measurements. More recently, Stephens [R. Stephens, J. Anal. At. Spectrom. 3, 1137 (1988)] has described an rf discharge between two metal electrodes at atmospheric pressure, operating in helium at a power of 5–30 W. The sputtering effect of the discharge was deduced by observing atomic emission from the plasma and atomic absorption within the plasma. Stephens pointed out that this device offered a convenient means of observing either emission or absorption for those elements for which sputtering was not inhibited by the presence of a stable oxide layer.

SUMMARY OF THE INVENTION

The invention pertains to a method of generating atom line emission or ion line spectra from a substance which comprises sustaining an atmospheric pressure plasma in a plasma containing volume having a pair of capacitively arranged electrodes enclosing at least a portion of the plasma containing volume, said electrodes being connected to a radio frequency generator and one of the electrode being insulated from the plasma, another of said electrode being constructed of the substance and penetrating into the plasma.

In the method the volume can be tubular, the first electrode can be cylindrical and encloses at least a portion of the tubular volume, and the second electrode can be constructed of the substance and penetrates axially into the tubular volume to an extent sufficient that there is an overlap between the first and second electrodes.

In the method the plasma can be operated at radio frequency input powers in the range of about 10 to about 600 W and can be supported with a flowing support gas. The support gas can be selected from the group consisting of Ar, He, $N_2$, $H_2$, air and mixtures of these gases. The plasma can be supported with a support gas flowing at a rate of about 0.05 L/m to about 10 L/m.

In the method the substance of the second electrode can be vaporized by the plasma discharge, thereby emitting atom lines and ion lines spectra characteristic of the substance which can be vaporized by rf sputtering. The support gas can be introduced into the plasma containing volume at a mid region of the volume while the electrode comprising the substance to be analyzed can be introduced into one end of the plasma containing volume.

The invention is also directed to an apparatus for generating atom line emission or ion line spectra from a substance to be analyzed which comprises: (a) hollow means adapted for containing and sustaining an atmospheric pressure capacitively generated plasma discharge; (b) a first electrode connected to a radio frequency power supply, electrically insulated from the plasma, enclosing at least a portion of the hollow means; and (c) a second electrode constructed of the substance to be analyzed, connected to a radio frequency power supply, and penetrating into the plasma discharge and being capacitively arranged with the first electrode.

In the apparatus the hollow means may be constructed of a high melting point electrically insulating material. The hollow means may be an elongated quartz tube. The second electrode may be elongated and penetrate axially into one end of the quartz tube. In the apparatus a support gas inlet may introduce plasma support gas into the hollow quartz tube.

In the apparatus the hollow quartz tube may be elongated, the first electrode may be in the form of a hollow elongated cylinder which can be arranged concentrically about at least a portion of the hollow cylindrical quartz tube and the second electrode may be in the form of a rod which penetrates axially into one end of the hollow quartz tube to an extent where there is overlap between the first electrode and a portion of the rod shaped electrode.

DRAWINGS

In the drawings, which illustrate specific embodiments of the invention, but which should not be regarded as limiting or restricting the spirit or scope of the invention in any way:

FIG. 1 depicts a schematic diagram of the CCP spectral lamp;

FIGS. 2a and 2b respectively depict recording of emission intensity of the Zn I 213.9 nm line in (1) HCL and (2) CCP spectral lamp;

FIGS. 3a and 3b respectively depict manganese emission spectra from HCL and CCP spectral lamp; and FIG. 4 depicts the Spectrum of an NBS 622 steel sample from the CCP spectral lamp.

DETAILED DESCRIPTION OF A SPECIFIC EMBODIMENT OF THE INVENTION

Description of the Spectral Lamp

Figure 4:
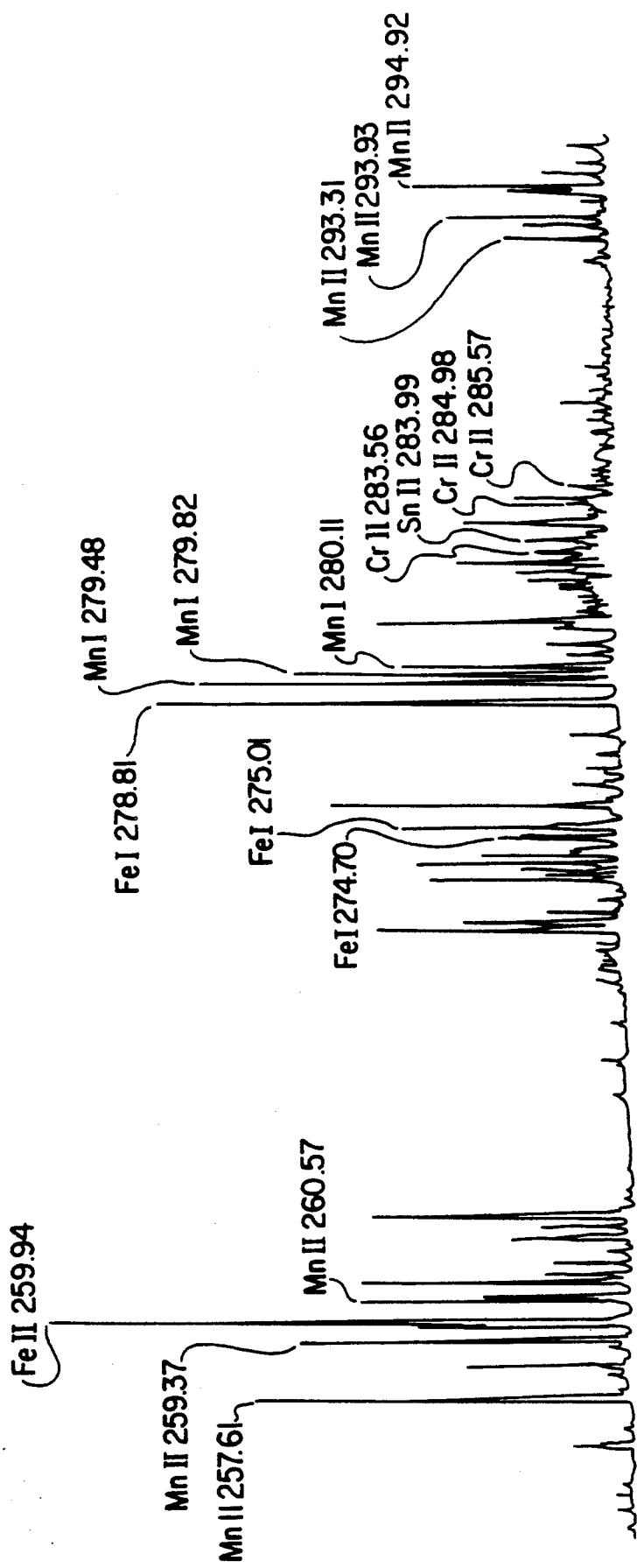

An atmospheric pressure rf capacitively coupled plasma (CCP) has been demonstrated in co-pending applications of the inventors, U.S. application Ser. No. 07/354,150, filed May 19, 1989, CAPACITIVELY COUPLED PLASMA DETECTOR FOR GAS CHROMATOGRAPHY, U.S. application Ser. No. 07/354,511, filed May 19, 1989, FURNACE ATOMIZATION ATMOSPHERIC PRESSURE CAPACITIVELY COUPLED PLASMA EXCITATION SOURCE, and U.S. application Ser. No. 07/378,263, filed July 11, 1989, AN ATMOSPHERIC PRESSURE CAPACITIVELY COUPLED PLASMA ATOMIZER FOR ATOMIC ABSORPTION AND EMISSION SPECTROSCOPY (the disclosure of which are incorporated herein by reference), to be a powerful tool in both atomic absorption spectrometry (AAS), atomic emission spectrometry (AES) and gas chromatography (GC). The discharge design provides for very effective energy transfer from the power supply to the plasma by capacitive coupling. Therefore, the plasma can be generated at atmospheric pressure and in a flexible geometry. The plasma can be operated over a wide range of rf input powers (10–600 W) which allows for optimal conditions for atom resonance line absorption and emission measurements.

A schematic diagram of the spectral lamp 2 is provided in FIG. 1. Functionally, the device 2 consists of three parts, the capacitively coupled plasma (CCP) discharge tube 4 sample electrode 6 and a cylindrical electrode 8 surrounding a portion of the tube 4. The main body of the tube 4 is constructed of quartz glass and includes a narrow neck 10 to form a T-shaped device. The neck 10 is hollow and provides an inlet for plasma support gas. The plasma 12 is contained in the quartz tube 4. Power is coupled into the plasma using electrodes 6 and 8. These electrodes 6 and 8 are connected to an RF power supply using equipment detailed in Table I.

The spectral lamp 2 was constructed of quartz glass with an internal diameter of about 0.65 cm and a wall thickness of 0.10 cm. A cylindrical stainless steel electrode 8, 7 cm in length and 0.9 cm in diameter, was placed around the outside of, and in contact with, the quartz tube 4. A central electrode 6 was inserted into a male B8 standard tapered quartz joint 14 and was sealed by two silicon rubber o-rings 16. The two quartz parts were connected together by a B8 standard quartz joint 14. The two electrodes 6 and 8 were connected to the output of an rf power supply. The outside electrode 4 and the central electrode 6 were overlapped by about 15 mm in length (see FIG. 1). This arrangement serves to increase the current density on the surface of the central electrode 6 and is important when high melting point metals are used as central electrodes.

Plasma support-gas was introduced through an inlet 10. This CCP lamp 2 can also work as an excitation source for direct solid analysis by replacing the central electrode 6 with electrically conducting sample rods as shown in U.S. application filed July 11, 1989, AN ATMOSPHERIC PRESSURE CAPACITIVELY COUPLED PLASMA ATOMIZER FOR ATOMIC ABSORPTION AND EMISSION SPECTROSCOPY. This lamp 2 has simple structure and can be easily made.

The plasma 12 has been operated using a fixed frequency 27.18 MH$_z$ RF supply and also with a 125–375 KH$_z$ variable frequency RF supply. It has been found that a stable plasma 12 can be sustained at RF powers ranging from 30–600 W. Plasma support gas is introduced using the inlet 10. It has been determined that the discharge will operate at gas flow rates ranging from 0.2 to 6 L/m. The plasma 12 has been sustained using a variety of support gases including Ar, He, and mixtures of these gases with N$_2$, H$_2$, and air.

In this disclosure, the term "lamp" is used to describe devices primarily designed to emit spectra for use as primary sources in Atomic Absorption Spectrometry (AAS) and atomic fluorescence spectrometry (AFS) as well as other optical measurements. By far the most important commercially available spectral lamp for AAS and AFS is the hollow cathode lamp (HCL). The main advantages of the HCL are its very small spectral line-width and its high signal to background ratio. However, the absolute intensity of emission from the HCL is relatively low compared with the radiation from other plasma sources. To overcome this problem, techniques such as direct current (dc) boosted-HCL, rf boosted-HCL, microwave coupled HCL, and high current pulsed HCL have been developed. Additionally, the intensities of ion lines in HCLs are very weak, due to the dominant population of ground state atom in glow discharges. One of factors is that traditional AAS primarily makes use of atomic resonance lines; however there is a large population of ground state analyte ions in inductively coupled plasmas (ICP's) even at relatively low powers.

The development of an intense ion line spectral source has some significance in this area in that it could assist in the reduction of source induced shot noise, consequently improving the detection limits for plasma source AAS. The intensities of the CCP spectral lamp 2 have been found to be up to 2-3 orders of magnitude greater than those from an HCL. The CCP spectral lamp 2 emits not only atom lines but also intense ion line spectra. Moreover, the lamp 2 can be used as a source for the direct analysis of solid samples without any significant structural modification. Its analytical performance has been demonstrated through the determination of manganese in steel samples using standard (NBS) low-alloy steel samples. This CCP lamp 2 allows for a wide selection of plasma conditions, good control of sampling and excitation, and ease of interchange of samples for direct solids analysis applications.

EXAMPLE

Comparison of Intensities of CCP Spectral Lamp and HCL

The equipment and experimental setup employed are summarized in Table I. Because the light emitted from the CCP spectral lamp and the HCL have different spatial shapes, and in order to eliminate possible error caused by poor alignment of optical elements, the optical system used for intensity comparison was set up without using any lenses. Both the CCP spectral lamps 2 and the HCLs are placed in the monochromator optical axis at a distance of 37 cm from the entrance slit. Before spectral measurements were made the positions of both lamps were optimized to give maximum signals.

Characteristics and Analytical Performance

The plasma in the CCP lamp 2 is very similar to those described in our co-pending patent applications except that the color of the plasma is modified by the components of the sample electrode 6. For the lamp 2, the plasma 12 fills the entire volume of the quartz tube 4 surrounded by the cylindrical electrode 8 including the overlap region between the two electrodes 6 and 8. At low rf power, the sample electrodes are dark or dark-red and atmospheric pressure rf sputtering is the dominant sampling mechanism. With an increase in rf power, the electrode color changes from orange to white-hot. Under this condition sampling takes place by a combination of both rf sputtering and thermal evaporation.

The effect of changes in rf input power on the emission intensity of the 213.9 nm Zn I line was studied at an argon flow rate of 0.63 L/m. The results over the power range 50-200 W are shown in FIG. 2. The emission intensity increases with an increase in rf power. When the rf power is increased above 75 W, the central electrode 6 becomes hot enough to cause thermal vaporization. In this case, the intensity increases dramatically. If the rf power was continuously increased to about 200 W, the brass electrode would melt down.

The intensities of resonance lines from the CCP spectral lamp and the HCL have been compared by the method outlined in the Example. The lamp operating parameters and the wavelengths of the resonance lines, as well as the emission intensity ratio of the CCP spectral lamp and the HCLs, are listed in Table II. Most of the HCL's were operated at the maximum currents specified by the manufacturers. The intensity measurements of zinc and copper for the CCP spectral lamp 2 were carried out by placing a brass central electrode 6 in the lamp; the intensity measurements of manganese, chromium and iron were carried out by using a stainless steel central electrode. All the resonance lines from the CCP spectral lamp 2 are one to two orders of magnitude stronger than those of the HCL's. Since the intensity differences of the CCP spectral lamp 2 and the HCL are so large, the intensity measurements were carried out at different photomultiplier tube (PMT) supply voltages. The log gain of the PMT has a linear relationship with the PMT supply voltages. This relationship was examined under the conditions of the experiment and was used for the normalization of the measurements. It is expected that larger intensity ratios can be obtained by using a pure metal rod as the central electrode 6.

Source induced PMT shot noise is one of the major noise sources in an atomic absorption spectrometer and contributes to the detection limit in AAS. In the case of shot noise, signal to noise ratios increase as the square root of source intensity. Therefore, the development of intense spectral lamps 6 is an important way to improve the detection limits for AAS. Rf electrodeless discharge lamps (EDL) have an intensity advantage over the HCL. However, they are only suited to excite a few elements with relatively high vapor pressures such as As, Cd, Hg, Pb, Sb, Se and Zn etc.. For example, the zinc EDL is one of the best EDL's, and is known to give an approximate intensity gain of 30 relative to the HCL. By comparison the CCP spectral lamp 2 with a brass central electrode is 369 times more intense compared with the zinc HCL. The high yield of atmospheric pressure sputtering is probably one of main causes for the high intensities of the CCP spectral lamps. A significant improvement of signal to noise ratio for the Zn I 213.9 nm line was found in the CCP spectral lamp 2 compared to the HCl as shown in FIGS. 2a and 2b, which respectively depict emission intensity of the Zn I 213.9 nm line in (1) HCL and (2) CCP lamps. Conditions: (1) Perkin-Elmer Zn HCL current—15 mA, PMT 900 V, recorder 1 V/F.S.; (2) CCP spectral lamp with brass central electrode (Cu—65%, Zn—35%): rf power 60 W, Ar flow rate 1.3 L/m, PMT 500 V, recorder 1 V/F.S. The content of zinc in the brass is approximately 30-35%. With a pure zinc central electrode and higher rf input power, higher emission intensity from Zinc would be obtained. On the other hand, the intensity advantage of the CCP spectral lamp provides for the possibility of intense multielement lamps by using metal alloys for the central electrode. As can be seen in Table II, the emission lines of Fe, Mn and Cr, from a stainless steel central electrode CCP spectral lamp, are significantly more intense than those of HCL's. When a multielement HCL is used, the detection limits usually become worse, due to the intensity loss in the multielement HCL's.

Typical emission intensities of manganese ion and atom lines in the CCP spectral lamp and the HCL are provided in FIGS. 3b and 3a, respectively depict the experimental conditions HCL: Perkin-Elmer Mn HCL, current—12 mA, PMT 900 V, Recorder 1 V/F.S.; CCP spectral lamp: rf power 200 W, Argon flow rate 0.7 L/m, PMT 500 V, recorder 5 V/F.S. The intensities of manganese ion lines are very weak in the HCL. The intensity ratio of Mn II 257.6 nm to the Mn I 279.5 nm line is 0.077 in the HCL and 0.77 in the CCP lamp. Since the material volatilized in a glow discharge is to a large extent present as a vapor cloud of free atoms, the small population of ions in HCL's results in very weak ion lines. Although the ion population in the CCP has not been measured, the intensity of Mn II 257.6 nm in the CCP spectral lamp 2 is about three orders of magnitude higher than that in the manganese HCL. Thus this lamp has potential as a source for use in ion line absorption spectroscopy (ICP-IAS for example).

The spectrum of the NBS 662 steel sample from the CCP spectral lamp 2 was recorded at an rf power of 150 W, and an argon gas flow rate of 1.2 L/m. The spectrum in the wavelength range 253–300 nm is provided in FIG. 4. Other than iron lines, the manganese triplet atom lines at 279.5, 279.8, and 280.1 nm, the manganese triplet ion lines at 257.6 nm, 259.4 and 260.6 nm, and the chromium ion lines at 283.6, 285.0, and 285.6 nm are present in this wavelength range. Mg I 285.2 nm, Pb I 283.3 nm and Sn I 284.0 nm lines were also observed. Due to the low resolution of the 0.35 m monochromator used in this research, it is difficult to eliminate the spectral overlap from these three lines. In addition, the chromium atom lines at 357.9, 359.4, and 360.5 nm, the copper atom lines at 324.8 and 327.4 nm, the silver atom lines at 328.1 and 338.3 nm; and the zinc atom line at 330.3 nm were found to be very intense in NBS 662. The concentrations of manganese, chromium, copper, silver and zinc in the NBS 662 sample are 1.05%, 0.3%, 0.51%, 0.001% and 0.0005% respectively. This indicates that it should be possible to use this configuration of the CCP for the direct analysis of impurities in conducting samples.

Iron Excitation Temperature

Temperature measurements were based on a two-line method. The two lines chosen were the Fe I 274.70 nm (E=43321 cm$^{-1}$, gf=0.40) lines shown in FIG. 4. These two lines fall in the same spectral region as the line pair for the manganese determination. It is convenient to record these two lines when carrying out the Mn determinations, since all four of the lines fall in the same dynamic range of the PMT. The temperature was measured at an rf input power of 150 W and a support gas flow rate of 1.3 L/min. From the intensities of Fe I 274.7 nm and Fe I 275.0 nm, the calculated temperature was found to be 5080±500 K.

TABLE I

| Experimental Facilities and Operating Conditions | |
|---|---|
| Plasma Power Supply | Perkin-Elmer ICP 5500 System consisting of a Plasma-Therm (Kreeson, N.J.), HFP-2500F RF generator, AMN-2500E automatic matching network, APCS-3 automatic power control system and PT - 2500 torch box. |
| Spectrometer | Schoeffel-McPherson (Acton, MA) Model 270, 0.35 m Czerny-Turner mount scanning monochromator with 1200 rulings/mm holographic grating, Reciprocal linear dispersion of 20 Å/mm in the first order. |
| Slits | Entrance and exit slits set to 50 μm for Mn determination, and 21 μm for intensity ratio measurement. |
| Hollow Cathode Lamps | Hollow cathode lamps (HCL) were powered using a dc power supply constructed at the University of British Columbia. |
| Detector Electronics | The photocurrent from a Hammatsu R955 photomultiplier tube was amplified by a preamplifier constructed at the University of British Columbia. The photomultiplier tube was powered using a McPherson Model EU-42A PMT power supply. |
| Data Acquisition | Digital data acquisition was carried out using a Tulsa Computers (Owasso, OK) Telex Model 1280 PC-AT compatible computer equipped with a an RC Electronics (Santa Barbara, CA) model ISC-16 analog-digital converter running the RC Computerscope software package. Analog data was acquired using a Servocorder 210 chart recorder. |

TABLE II

Intensity Ratio of resonance Line of CCP Lamp and HCL

| Elememt | Wavelength (nm) | Operating Parameter of CCP lamp | Operating Parameter of HCL | Ratio (CCP/HCL) |
|---|---|---|---|---|
| ZN | 213.86 | rf power: 60 w flow rate: 1.3 L/min | P-E lamp d.c.: 15 mA | 369 |
| Fe | 248.33 | rf power: 250 w flow rate: 0.3 L/min | P-E lamp d.c.: 12 mA | 246 |
| Mn | 279.48 | rf power: 250 w flow rate: 0.3 L/min | P-E lamp d.c.: 12 mA | 84 |
| Cr | 357.87 | rf power: 250 w flow rate: 0.3 L/min | P-E lamp d.c.: 15 mA | 13 |
| Cu | 324.75 | rf power: 60 w flow rate: 1.3 L/min | Hamamatsu lamp d.c.: 3 mA | 13 |

As will be apparent to those skilled in the art, in the light of the foregoing disclosure, many alterations and modifications are possible in the practice of this invention without departing from the spirit or scope thereof. Accordingly, the scope of the invention is to be construed in accordance with the substance defined by the following claims.

We claim:

1. A method of generating atom line or ion line spectra from a substance which comprises sustaining an atmospheric pressure plasma in a plasma containing volume having first and second capacitively arranged electrodes enclosing at least a portion of the plasma containing volume, said first and second electrodes being connected to a radio frequency generator and said first electrode being insulated from the plasma, said second electrode being constructed of the substance, said second electrode penetrating into the plasma so that there is an overlap between the second electrode and the first electrode.

2. A method of generating atom line or ion line spectra from a substance, which method comprises sustaining an atmospheric pressure plasma in a plasma containing volume having first and second capacitively arranged electrodes enclosing at least a portion of the plasma containing volume, said electrodes being connected to a radio frequency generator and said first electrode being insulated from the plasma, and wherein the volume is tubular, the first electrode is cylindrical and encloses at least a portion of the tubular volume, and the second electrode is constructed of the substance and penetrates axially into the tubular volume to an extent sufficient that there is an overlap between the second electrode and the first electrode.

3. A method as defined in claim 2 wherein the plasma is operated at radio frequency input powers in the range of about 10 to about 600 W.

4. A method as defined in claim 3 wherein the plasma is supported with a flowing support gas.

5. A method as defined in claim 4 wherein the support gas is selected from the group consisting of Ar, He, $N_2$, $H_2$, air and mixtures of these gases.

6. A method as defined in claim 4 wherein the plasma is supported with a support gas flowing at a rate of about 0.05 L/m to about 10 L/m.

7. A method as defined in claim 4 wherein the substance of the second electrode is vaporized by the plasma discharge, thereby emitting atom lines and ion lines spectra characteristic of the substance.

8. A method as defined in claim 7 wherein the substance is vaporized by atmospheric pressure rf sputtering.

9. An apparatus for generating atom line emission or ion line spectra from a substance to be analyzed which comprises:
   (a) hollow means for containing and sustaining an atmospheric pressure capacitively generated plasma discharge;
   (b) a first electrode connected to a radio frequency power supply, electrically insulated from the plasma, and enclosing at least a portion of the hollow means; and
   (c) a second electrode constructed of the substance to be analyzed, connected to a radio frequency power supply, and being capacitively arranged with the first electrode, and penetrating into the interior of the hollow means and plasma discharge to an extent that there is an overlap between the first electrode and the second electrode.

10. An apparatus as defined in claim 9 wherein the hollow means is constructed of a high melting point electrically insulating material.

11. An apparatus as defined in claim 10 wherein the hollow means is an elongated quartz tube.

12. An apparatus for generating atom line emission or ion line spectra from a substance to be analyzed which comprises:
   (a) a hollow quartz tube for containing and sustaining an atmospheric pressure capacitively generated plasma discharge;
   (b) a first electrode connected to a radio frequency power supply, electrically insulated from the plasma, and enclosing at least a portion of the quartz tube; and
   (c) a second electrode constructed of the substance to be analyzed, connected to a radio frequency power supply, and capacitively arranged with the first electrode, and wherein the second electrode is elongated and penetrates axially into one end of the quartz tube.

13. An apparatus as defined in claim 12 wherein a support gas inlet introduces plasma support gas into the hollow quartz tube.

14. An apparatus as defined in claim 13 wherein the hollow quartz tube is elongated, the first electrode is in the form of a hollow elongated cylinder which is arranged concentrically about at least a portion of the hollow cylindrical quartz tube and the second electrode is in the form of a rod which penetrates axially into one end of the hollow quartz tube to an extent wherein there is overlap between the first electrode and a portion of the rod shaped electrode.

* * * * *